US011123049B2

(12) United States Patent
Kramer et al.

(10) Patent No.: US 11,123,049 B2
(45) Date of Patent: Sep. 21, 2021

(54) SYSTEM FOR COLLECTING BIOMATERIAL IN A VESSEL

(71) Applicant: WK Holdings, Inc., Monroe, NY (US)

(72) Inventors: Heidi Kramer, Monroe, NY (US);
Herman Wagschal, Monroe, NY (US);
Joseph Wagschal, Monroe, NY (US)

(73) Assignee: WK HOLDINGS, INC., Monroe, NY (US)

( * ) Notice: Subject to any disclaimer, the term of this patent is extended or adjusted under 35 U.S.C. 154(b) by 0 days.

(21) Appl. No.: 15/803,205

(22) Filed: Nov. 3, 2017

(65) Prior Publication Data

US 2018/0055489 A1 Mar. 1, 2018

Related U.S. Application Data

(63) Continuation of application No. PCT/US2015/060181, filed on Nov. 11, 2015, which
(Continued)

(51) Int. Cl.
*A61B 10/00* (2006.01)
*G01N 33/50* (2006.01)
(Continued)

(52) U.S. Cl.
CPC ............ *A61B 10/007* (2013.01); *A61B 90/90* (2016.02); *B01L 3/508* (2013.01); *B01L 3/50853* (2013.01);
(Continued)

(58) Field of Classification Search
None
See application file for complete search history.

(56) References Cited

U.S. PATENT DOCUMENTS 3,571,817 A    3/1971    Gosnell
3,815,646 A *   6/1974    Coakley .................. B67C 11/02
                                                                       141/337
(Continued)

FOREIGN PATENT DOCUMENTS

JP      62-111035 A    7/1987
JP      5-209996 A     8/1993
(Continued)

OTHER PUBLICATIONS

International Search Report and Written Opinion of the International Searching Authority for corresponding International Patent Application No. PCT/US2015/060181 dated Feb. 3, 2016, 6 pages.
(Continued)

*Primary Examiner* — Matthew Kremer
(74) *Attorney, Agent, or Firm* — Merchant & Gould P.C.

(57) ABSTRACT

A system for hands-free collection of biomaterials, such as urine, in a vessel disposed below a closable port, the vessel being sealable by an at least partially automated sealing mechanism, the sealed vessel being transferable to a storage area. In general terms this application is directed to a hands-free, biomaterial collection system that is it least partially automated. In one aspect, a biomaterial collection system comprises a biomaterial capture area including a port, a collection area disposed below the capture area, a vessel disposed in the collection area and aligned with the port, and a sealing mechanism disposed in the collection area for sealing the vessel.

19 Claims, 11 Drawing Sheets

Related U.S. Application Data is a continuation-in-part of application No. 14/704,034, filed on May 5, 2015, now Pat. No. 9,974,520, application No. 15/803,205, which is a continuation-in-part of application No. 14/704,034, filed on May 5, 2015, now Pat. No. 9,974,520.

(60) Provisional application No. 61/989,210, filed on May 6, 2014.

(51) Int. Cl.
  *B01L 3/00* (2006.01)
  *E03D 13/00* (2006.01)
  *E03D 11/00* (2006.01)
  *A61B 90/90* (2016.01)

(52) U.S. Cl.
  CPC ............ *E03D 11/00* (2013.01); *E03D 13/005* (2013.01); *G01N 33/50* (2013.01); *B01L 2200/0689* (2013.01); *B01L 2200/141* (2013.01); *B01L 2300/04* (2013.01)

(56) References Cited

U.S. PATENT DOCUMENTS

| | | |
|---|---|---|
| 3,943,770 A | 3/1976 | McDonald |
| 4,064,760 A | 12/1977 | Benjamin |
| 4,067,335 A * | 1/1978 | Silvanov ............... A61F 5/455 604/328 |
| 4,252,132 A | 2/1981 | Kuntz |
| 4,301,812 A | 11/1981 | Layton et al. |
| 4,495,951 A | 1/1985 | Kenda |
| 4,569,090 A | 2/1986 | Muller |
| 4,636,474 A | 1/1987 | Ogura et al. |
| 4,705,085 A * | 11/1987 | Brown ............... B65D 81/3881 206/522 |
| 4,860,767 A | 8/1989 | Maekawa |
| 4,901,736 A | 2/1990 | Huang |
| 4,961,431 A | 10/1990 | Ikenaga et al. |
| 4,962,550 A | 10/1990 | Ikenaga et al. |
| 5,073,500 A | 12/1991 | Saito et al. |
| 5,105,824 A | 4/1992 | Rasch |
| 5,111,539 A | 5/1992 | Hiruta et al. |
| 5,184,359 A | 2/1993 | Tsukamura et al. |
| 5,198,192 A | 3/1993 | Saito et al. |
| 5,410,471 A | 4/1995 | Alyfuku et al. |
| 5,652,911 A | 7/1997 | Van Venrooy et al. |
| 5,714,033 A | 2/1998 | Hayashi et al. |
| 5,720,054 A | 2/1998 | Nakayama et al. |
| 5,730,149 A | 3/1998 | Nakayama et al. |
| 5,745,926 A | 5/1998 | Cailleteau |
| 5,758,917 A * | 6/1998 | Langley ............... A01K 23/005 15/257.8 |
| 5,785,044 A | 7/1998 | Meador |
| 5,920,916 A | 7/1999 | Norton |
| 6,052,842 A | 4/2000 | He |
| 6,079,058 A * | 6/2000 | Green ............... A47K 11/045 4/479 |
| 6,294,046 B1 | 9/2001 | Kume et al. |
| 6,342,704 B1 | 1/2002 | Jen et al. |
| 6,358,477 B1 | 3/2002 | Webb et al. |
| 6,402,702 B1 | 6/2002 | Gilcher et al. |
| 6,493,884 B1 | 12/2002 | Muller et al. |
| 6,572,564 B2 | 6/2003 | Ito et al. |
| 6,607,166 B1 * | 8/2003 | Pichkhadze ............... B64D 1/14 244/138 R |
| 6,684,414 B1 | 2/2004 | Rehrig |
| 6,775,852 B1 | 8/2004 | Alvarez et al. |
| 6,852,288 B2 | 2/2005 | Newberg |
| 7,195,602 B2 | 3/2007 | Yong et al. |
| 7,229,409 B2 | 6/2007 | Ito et al. |
| 7,291,309 B2 | 11/2007 | Watson et al. |
| 7,454,881 B2 | 11/2008 | Hanatani et al. |
| 7,785,304 B2 | 8/2010 | Kashmiran et al. |
| 7,819,821 B2 | 10/2010 | Forte et al. |
| 7,846,384 B2 | 12/2010 | Watson et al. |
| 8,328,733 B2 | 12/2012 | Forte et al. |
| 8,690,794 B1 | 4/2014 | Gallardo |
| 9,149,163 B2 | 10/2015 | Natt et al. |
| 9,155,525 B2 | 10/2015 | Lipinsky et al. |
| 2002/0193762 A1 | 12/2002 | Suydam |
| 2004/0138587 A1 * | 7/2004 | Lyons, IV ........ A61B 17/00234 600/562 |
| 2005/0004538 A1 | 1/2005 | Forte |
| 2005/0142041 A1 | 6/2005 | Newberg |
| 2005/0261605 A1 | 11/2005 | Shermer et al. |
| 2007/0006368 A1 | 1/2007 | Key |
| 2007/0044213 A1 | 3/2007 | Hall |
| 2007/0270716 A1 | 11/2007 | Wu et al. |
| 2008/0312636 A1 * | 12/2008 | Miller ................ A61B 17/3415 604/508 |
| 2009/0089919 A1 | 4/2009 | Rudolph |
| 2009/0216099 A1 | 8/2009 | Kim |
| 2009/0255045 A1 * | 10/2009 | Sakurai ................ A47K 11/026 4/484 |
| 2010/0269250 A1 | 10/2010 | Wilson et al. |
| 2010/0288059 A1 | 11/2010 | Viljoen et al. |
| 2010/0031381 A1 | 12/2010 | Cook |
| 2011/0051125 A1 | 3/2011 | Kim |
| 2011/0139276 A1 | 6/2011 | Kashmiran et al. |
| 2012/0046574 A1 | 2/2012 | Skakoon |
| 2013/0139474 A1 | 6/2013 | Coleman |
| 2014/0216598 A1 | 8/2014 | Kashmiran et al. |
| 2014/0276214 A1 | 9/2014 | Lipinsky et al. |
| 2015/0223783 A1 | 8/2015 | Eschete et al. |
| 2015/0320404 A1 | 11/2015 | Kramer |
| 2015/0359522 A1 | 12/2015 | Recht et al. |

FOREIGN PATENT DOCUMENTS

| | | |
|---|---|---|
| JP | 8-15255 A | 6/1994 |
| WO | 95/18373 A1 | 7/1995 |
| WO | 95/23337 A1 | 8/1995 |
| WO | 96/09794 A1 | 4/1996 |
| WO | 97/08993 A2 | 3/1997 |
| WO | 97/27795 A1 | 8/1997 |
| WO | 99/28724 A1 | 6/1999 |
| WO | 99/59874 A1 | 11/1999 |
| WO | 02/09493 A1 | 2/2002 |
| WO | 02/26096 A1 | 4/2002 |
| WO | 02/094104 A1 | 11/2002 |
| WO | 03/007771 A1 | 1/2003 |
| WO | 2004/036343 A2 | 4/2004 |
| WO | 2005/048842 A1 | 6/2005 |
| WO | 2007/009170 A1 | 1/2007 |
| WO | 2008/065325 A1 | 6/2008 |
| WO | 2009/107988 A2 | 9/2009 |
| WO | 2009/129638 A2 | 10/2009 |
| WO | 2010/132800 A1 | 11/2010 |
| WO | 2011/113164 A2 | 9/2011 |
| WO | 2011/144950 A1 | 11/2011 |
| WO | 2012/011127 A1 | 1/2012 |
| WO | 2014/152626 A2 | 9/2014 |

OTHER PUBLICATIONS

European Search Report dated Feb. 5, 2019 in EP Application No. 15891393.

* cited by examiner

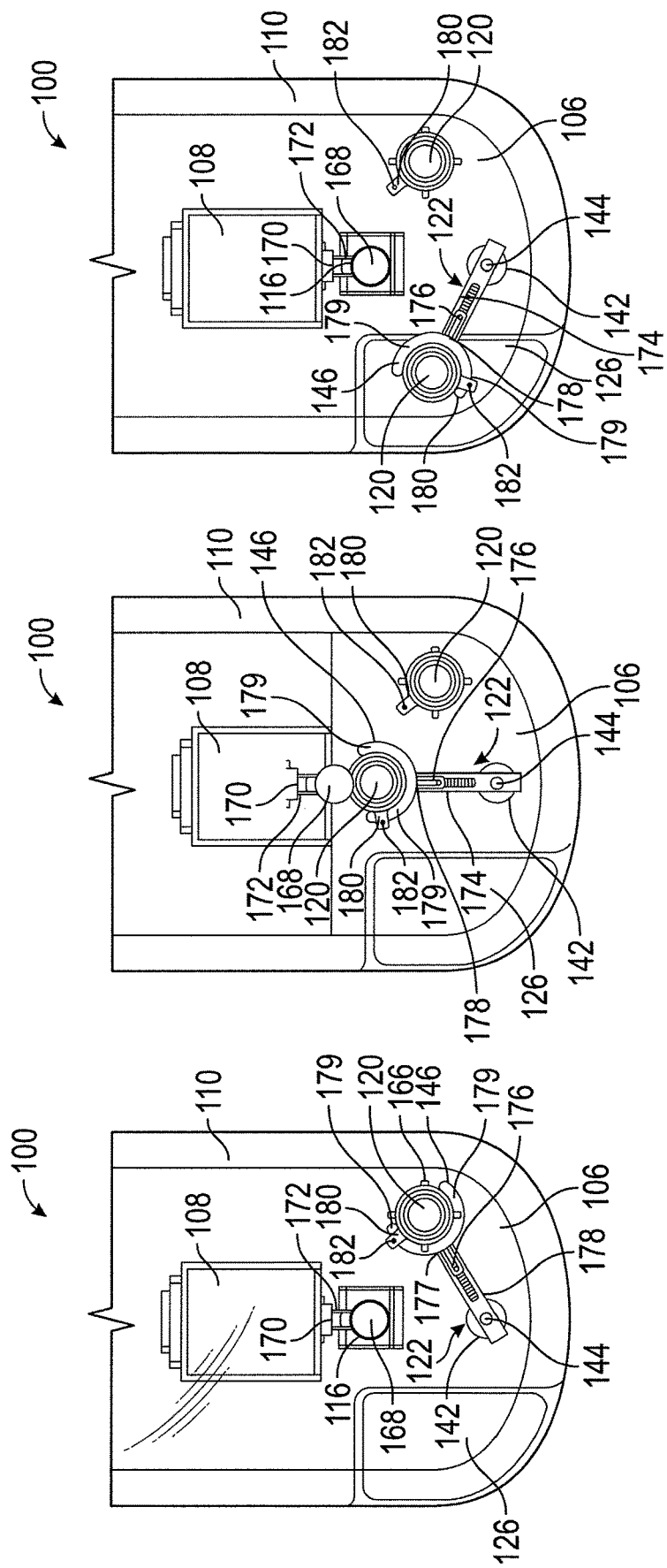

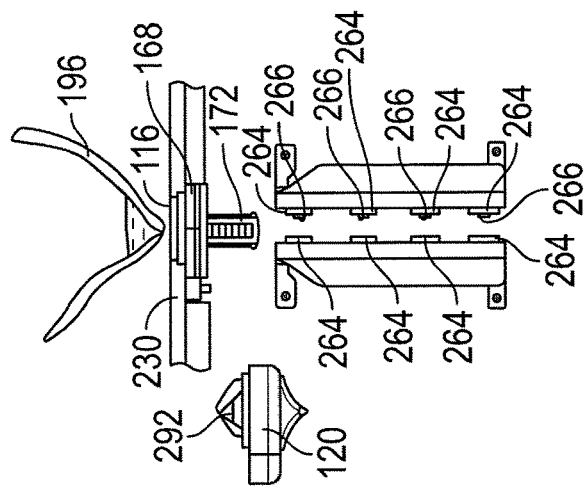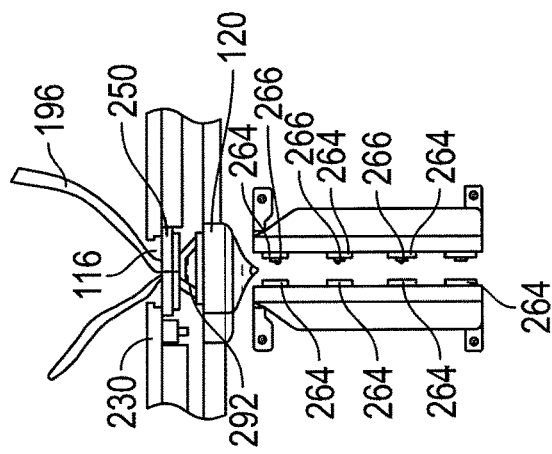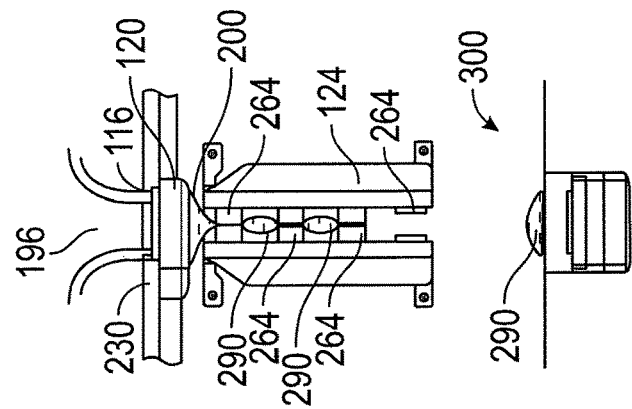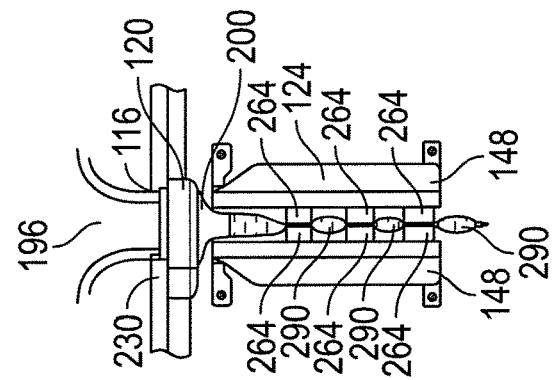

SYSTEM FOR COLLECTING BIOMATERIAL IN A VESSEL

CROSS-REFERENCE TO RELATED APPLICATIONS

This application is a Continuation Application of PCT/US2015/060181, filed on Nov. 11, 2015, which claims priority to U.S. patent application Ser. No. 14/704,034 filed on May 5, 2015, now U.S. Pat. No. 9,974,520, the disclosure of which is incorporated herein by reference in its entirety. This application is also a Continuation-In-Part Application of U.S. patent application Ser. No. 14/704,034, which claims the benefit under 35 U.S.C. 119 of U.S. Provisional Patent Application No. 61/989,210, filed May 6, 2014, the disclosure of which is hereby incorporated by reference in its entirety. The U.S. designation of International PCT Application PCT/US2015/060181 also claims priority to U.S. Provisional Patent Application No. 61/989,210.

BACKGROUND

Biomaterials (e.g., urine, blood, feces) are routinely collected by medical and other professionals to test for any of a variety of biological conditions, diseases, drug or alcohol impairment, and so forth.

There is a need for improved systems for the collection and/or processing of biomaterial samples.

SUMMARY

In general terms this application is directed to a hands-free, biomaterial collection system that is it least partially automated.

In one aspect, a biomaterial collection system comprises a biomaterial capture area including a port, a collection area disposed below the capture area, a vessel disposed in the collection area and aligned with the port, and a sealing mechanism disposed in the collection area for sealing the vessel.

In another aspect a biomaterial collection system comprises a biomaterial capture area including a port, a collection area disposed below the capture area, an inflatable vessel disposed in the collection area and aligned with the port, a sealing mechanism disposed in the collection area for sealing the vessel, and an inflatable funnel disposed at least partially above the port.

In a further aspect, a biomaterial collection system comprises a waste receptacle having a drain, a biomaterial capture area including a port, a storage area for storing sealed, collected samples of biomaterial, and a collection area disposed below the capture area, a vessel disposed in the collection area and aligned with the port, and a sealing mechanism disposed in the collection area for sealing the vessel.

In yet a further aspect, a biomaterial collection system comprises a biomaterial capture area including a port, a collection area disposed below the capture area, at least one collection unit containing an inflatable and detachable vessel disposed in the collection area and a detachable funnel disposed in the capture area, the system further comprising a sealing mechanism disposed in the collection area for sealing and cutting the vessel into a plurality of discrete packets of biomaterial, the system further comprising a transport mechanism for transporting the at least one collection unit between a storage position, a biomaterial collecting position, and a disposal position, the system further comprising a printer for labeling the discrete packets of biomaterial with information identifying a source of the biomaterial, the system further comprising a chilled storage unit for preserving the sealed and labeled packets of biomaterial, and a conveyor for transporting the packets of biomaterial to the chilled storage unit.

BRIEF DESCRIPTION OF THE FIGURES

FIG. 4A is a top view of a portion of the collection system of FIG. 1, illustrating the grasping element of the transport mechanism in a first position.

FIG. 4B is a top view of a portion of the collection system of FIG. 1, illustrating the grasping element of the transport mechanism in a second position.

FIG. 4C is a top view of a portion of the collection system 100 of FIG. 1, illustrating the grasping element of the transport mechanism in a third position.

FIG. 9A is a side view representation of an example sealing mechanism and collection unit of FIG. 1 at a first time following collection of a subject's urine.

FIG. 9B is a side view representation of an example sealing mechanism and the collection unit of FIG. 1 at a second time following the first time of FIG. 9B.

FIG. 9C is a side view representation of the example sealing mechanism and the collection unit of FIG. 1 at a third time following the second time of FIG. 9B.

FIG. 9D is a side view representation of the example sealing mechanism and the collection unit of FIG. 1 at a fourth time following the third time of FIG. 9C.

DETAILED DESCRIPTION

Figure 1:
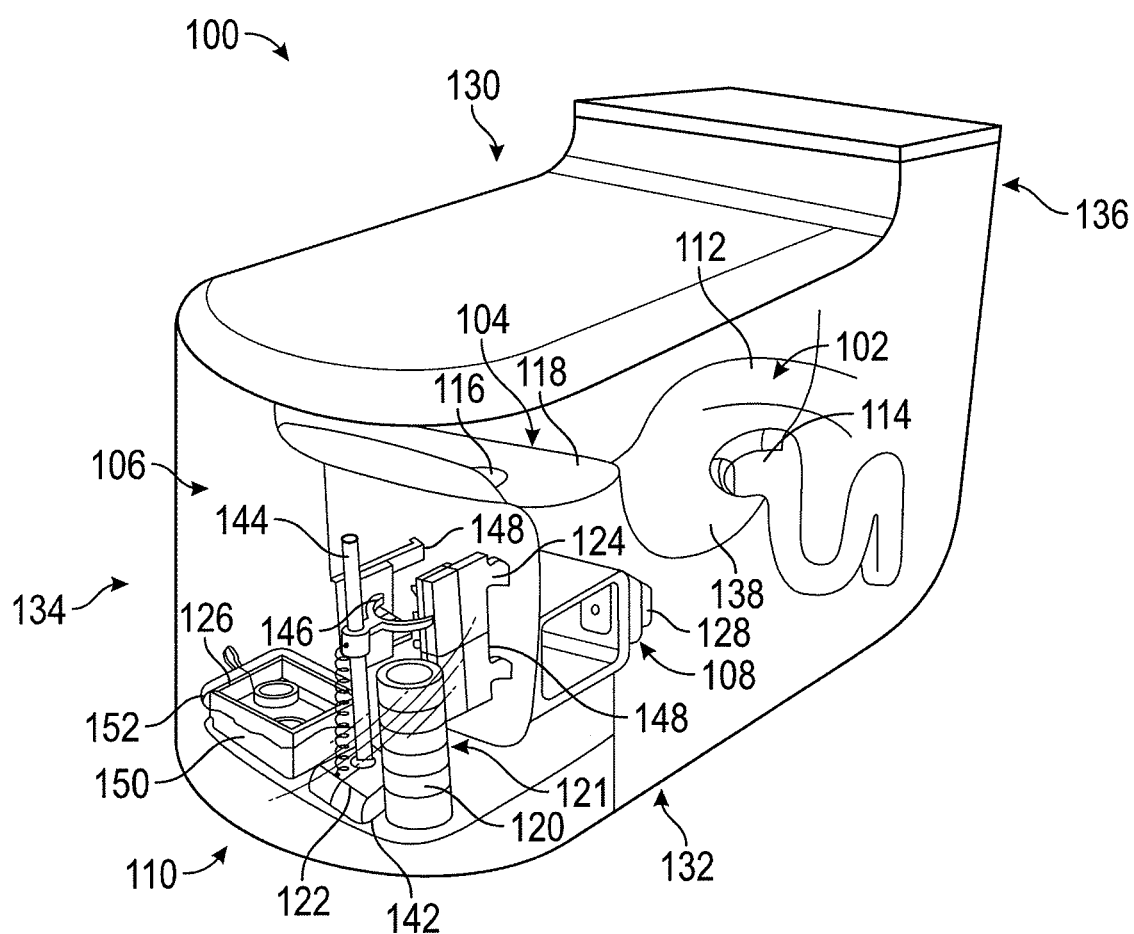
FIG. 1 is a perspective view of a urine collection system in accordance with the present disclosure, showing various interior components of the collection system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

As used throughout this disclosure, biomaterials include any biological substance produced by humans. Non-limiting examples of biomaterials include blood, urine, saliva, semen, feces, sweat and so forth. The biomaterial collection system embodiments of the present disclosure will be described with particular reference to the collection of urine from a human subject. However, it should be appreciated that principles of the embodiments described herein may be readily applied to the collection of other biomaterials.

FIG. 1 is a perspective view of a urine collection system 100 in accordance with the present disclosure, showing various interior components of the collection system 100.

The collection system 100 includes a waste receptacle 102, a capture area 104, a collection area 106, and a storage area 108. A housing unit 110 houses the waste receptacle 102, the capture area 104, the collection area 106 and the storage area 108. The waste receptacle 102 includes a reservoir 112 and a drain 114. The capture area 104 includes a closable port 116. In some examples, the closable port 116 is disposed in a sloped surface 118 of the capture area 104. Disposed in the collection area 106 is one or more collection units 120, a transport mechanism 122, a sealing mechanism 124, and a waste area 126. In this example, the storage area 108 includes a storage container 128.

In some examples, the collection system 100 provides an automated or partially automated system for the collection of urine for testing purposes. In some examples the collection system 100 is configured to collect urine samples from a sequence of multiple subjects with little or no involvement from a human operator (e.g., a medical professional) in between successive subjects' urination, the system being configured to reduce or prevent cross-contamination from one subject's urine sample to another subject's urine sample, and also configured to identify each collected sample by associating with the appropriate subject.

In some examples, the collection system 100 includes one or more automated sterilizing components that sterilize shared aspects of the collection system 100 in between subjects' urination. In some examples, the collection system 100 includes a sterilizing mechanism, e.g., an ultraviolet light generator and/or a steam generator to sterilize one or more components of the collection system 100 between usages by successive subjects providing urine samples.

The collection system 100 is generally defined by a top 130, a bottom 132, a front 134 and a back 136. The top 130 and the bottom 132 generally define vertical planes through the collection system 100, while the front 134 and the back 136 generally define horizontal planes through the collection system 100. In some examples, the collection system 100 is connected to a plumbing or septic system for disposal of human or other waste via the drain 114. For example, the waste receptacle 102 and drain 114 can function as a conventional toilet. An opening at the top 130 of the collection system 100 allows fluid access (e.g., by urinating) to the waste receptacle 102 and the capture area 104.

The waste receptacle 102 includes a recessed portion 138 and the drain 114. In some examples, the waste receptacle 102 contains a liquid (e.g., water) and the drain 114 includes a valve for selectively draining the liquid and/or any waste material from the waste receptacle 102, e.g., with a toilet flushing mechanism. In some examples the recessed portion 138 is recessed relative to the sloped surface 118 of the capture area 104 such that fluid that contacts the sloped surface 118 runs off (via the force of gravity) into the waste receptacle 102.

In the embodiment shown, the capture area 104 is disposed forward of (i.e., towards the front 134) of the waste receptacle 102, which can facilitate the capture of urine during urination. In other examples, the capture area 104 can be behind, beside or directly above the waste receptacle 102. The capture area 104 is defined by an open state and a closed state. In the open state, the closable port 116 is open, allowing for communication between the capture area 104 and the collection area 106. In the closed state, the closable port 116 is closed providing a fluid seal between the capture area 104 and the collection area 106, such that no fluid (e.g., urine) entering the capture area 104 passes through the port 116.

The collection area 106 is generally disposed below (i.e., towards the bottom 132) the capture area 104, enabling the collection area 106 to receive urine via the port 116 from the capture area 104. The collection area 106 contains one or more collection units 120, e.g., in a stacked configuration.

Each collection unit 120 is configured to collect a single subject's urine for testing or other processing. In the embodiment shown, each collection unit 120 of the stack 121 of collection units has a compact configuration prior to using the collection unit 120 to collect urine. In the compact configuration, a collection element of a collection unit 120 is enclosed by a casing 140 (see FIG. 5A). The casing 140 protects the collection element (e.g., the vessel 200 and the funnel 196 discussed below) from contamination prior to use, and allows a handler of the collection system 100 to purchase and store collection units 120 outside of the collection system 100, and replenish the collection system 100 with fresh collection units 120 without contaminating the collection element enclosed within.

The transport mechanism 122 includes a base 142, a shaft 144 and a grasping element 146. The base 142 is coupled to an interior surface of the collection area 106. The shaft 144 extends upwards from the base 142. The grasping element 146 is configured to releasably grasp a collection unit 120. The grasping element 146 is also configured for translational movement relative to the shaft 144 (e.g., up and down the shaft 144) and/or rotational movement about the shaft 144 (see the arrows in FIG. 1). In some examples, the grasping element 146 and the shaft 144 are threadably coupled to each other (e.g., similar to a nut and screw coupling), allowing controlled rotational and translational movement of the grasping element 146 relative to the shaft 144 (e.g., by screw action), without slippage of the grasping element 146 down the shaft 144.

When the grasping element 146 is grasping a collection unit 120, the grasping element 146 can selectively or automatically transport the collection unit 120 translationally and/or rotationally about the shaft 144. In a first position of the grasping element 146, the grasping element 146 is at least approximately vertically aligned with the stack 121 of the collection units 120 (see FIG. 4A). In a second position of the grasping element 146, the grasping element 146 is at least approximately vertically aligned with the port 116 (see FIG. 4B). In a third position of the grasping element 146, the grasping element 146 is at least approximately vertically aligned with the waste area 126 (see FIG. 4C). Movement of the grasping element 146 can be accomplished by any suitable means, e.g., with a motor coupled to an actuator and/or with hydraulics. In some examples, the base 142 includes a motive element for driving the grasping element 146. That is, the motive element communicates with the grasping element to provide rotational, translational, and grasping/releasing movement of the grasping element 146. Control of the motive element can be accomplished with an electronic controller having an interface on the collection system 100 or remotely therefrom.

The sealing mechanism 124 is disposed below the capture area 104. In some examples, the sealing mechanism 124 includes first and second arms 148. In some examples the first and second arms 148 are movable between an open configuration and a closed configuration. In other examples, the arms 148 are fixed in the same relative position while one or more heated projections extend and retract therefrom to move the sealing mechanism 124 between the open and closed configurations, as discussed in more detail below in connection with FIGS. 8-9. In moving from the open configuration to the closed configuration the first and second arms pinch or squeeze a urine collection vessel (described in more detail below) in one or more locations to seal the collection vessel in one or more locations.

The waste area 126 is disposed within the collection area 106 and is configured to receive one or more portions of used collection units 120 after collection is complete. In some examples, the waste area 126 includes a receptacle 150 lined with a disposable, liquid proof bag 152 for hygienic removal of the used collection units 120 from the collection system 100. In use, the grasping element 146 of the transport mechanism 122 grasping a used collection unit 120 rotates about the shaft 144 until the used collection unit 120 is above the waste area 126. At this point, the grasping element 146 releases the used collection unit 120, which drops (via the force of gravity) into the waste area 126.

The storage area 108 receives sealed urine samples that have been collected. In some examples the storage area 108 includes a refrigerated storage container 128 to preserve the collected urine specimens until retrieval is desired. The storage container 128 can include a refrigeration unit and a door for accessing sealed urine samples in the storage container 128.

Figure 2A:
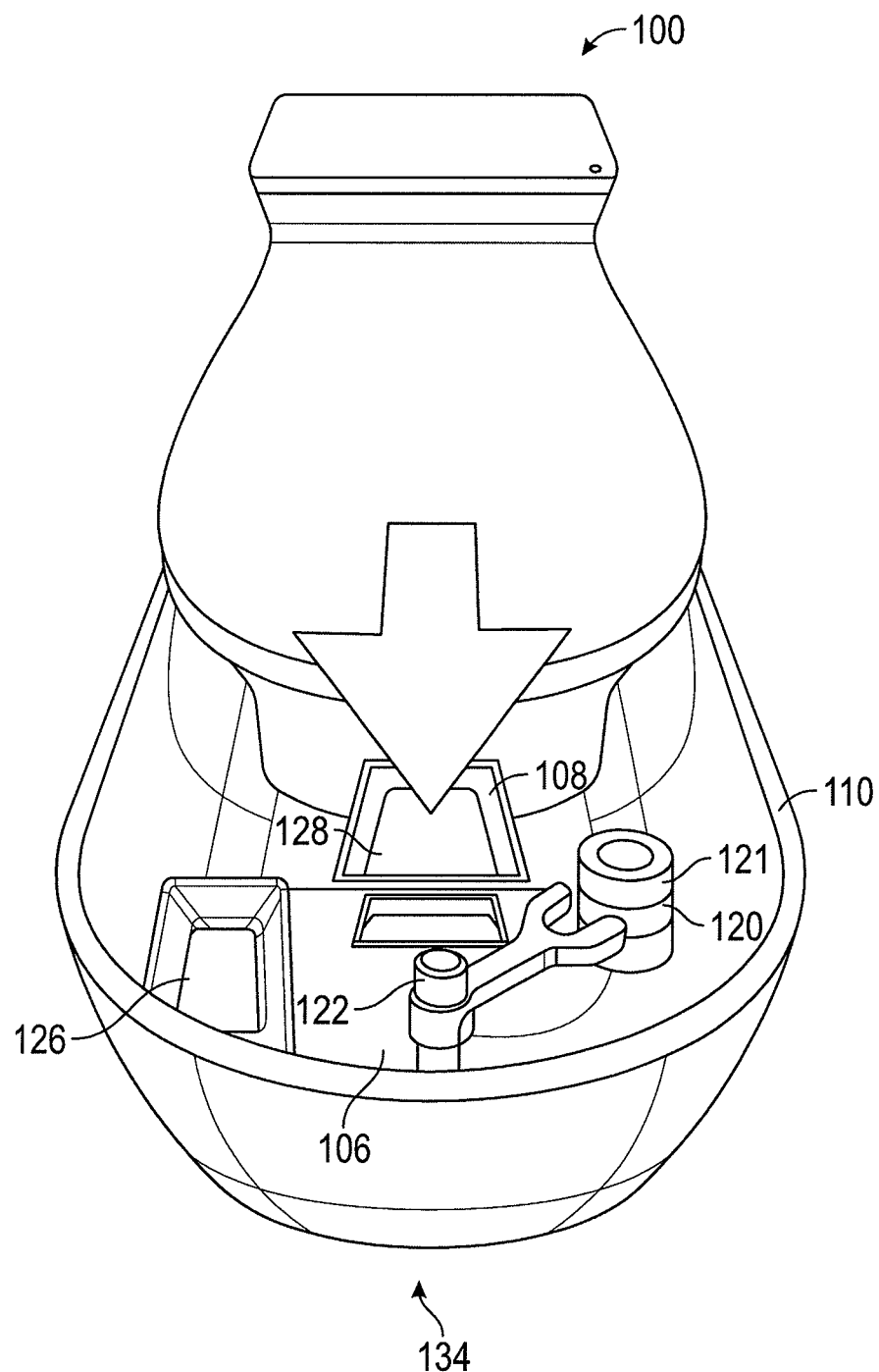
FIG. 2A is a top perspective view of a portion of the collection system of FIG. 1 illustrating the housing unit of FIG. 1 in a retrieval configuration.
Figure 2B:
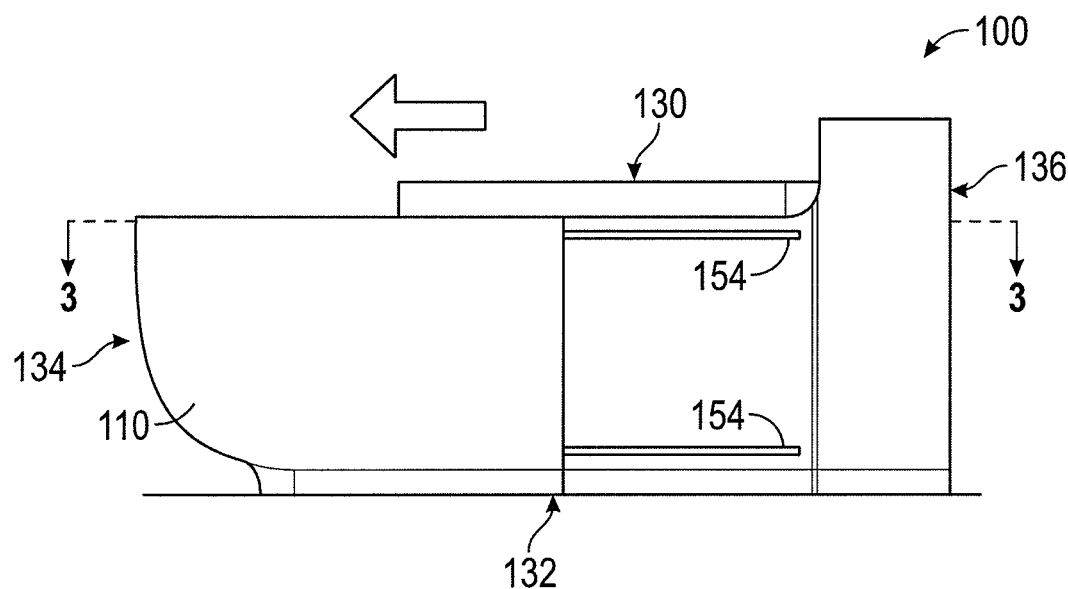
FIG. 2B is a side view of the collection system of FIG. 1 illustrating the housing unit of FIG. 1 in a retrieval configuration.

FIG. 2A is a top perspective view of a portion of the collection system 100 of FIG. 1 illustrating the housing unit 110 of FIG. 1 in a retrieval configuration. FIG. 2B is a side view of the collection system 100 of FIG. 1 illustrating the housing unit 110 of FIG. 1 in a retrieval configuration. With reference to FIGS. 2A and 2B, the collection system 100 includes the collection area 106, the storage area 108, the housing unit 110, the stack 121 of unused collection units 120, the transport mechanism 122, the waste area 126 and the storage container 128, the collection system 100 having the top 130, the bottom 132, the front 134, and the back 136 as described above.

As illustrated in FIGS. 2A and 2B, in some examples of the collection system 100, the housing unit 110 has a retrieval configuration, allowing access to the collection area 106, the storage area 108 and the waste area 126. Thus, for example, in the retrieval configuration, sealed urine samples and used collection units 120 can be retrieved from the housing unit 110, and fresh collection units 120 can be replenished. In addition, the retrieval configuration can allow for maintenance or replacement of one or more of the components housed in the housing unit 110. To achieve the retrieval configuration, in some examples the housing unit 110 is slidable (e.g., with wheels or rollers along the floor) relative to the rest of the collection system 100. The retrieval configuration can be achieved manually and/or alternatively with an electrically driven driver. In some examples, the housing unit 110 slides along one or more tracks 154 (FIG. 2B). It should be appreciated that the housing unit 110 need not slide along the front to back direction as depicted in FIG. 2. For example, the housing unit 110 can be configured to slide side to side. Precisely how the housing unit achieves the retrieval configuration can be customized according to the room in which the collection system 100 is situated, to allow easier access to the interior of the housing unit 110 in the retrieval configuration.

To return the collection system 100 to its operating mode, the housing unit 110 is moved back to its original position relative to the rest of the collection system 100. In alternative embodiments, access to the interior of the housing unit 110 can be accomplished by alternative means, e.g., via one or more doors or flaps on one or more sides of the housing unit 110.

Figure 3:
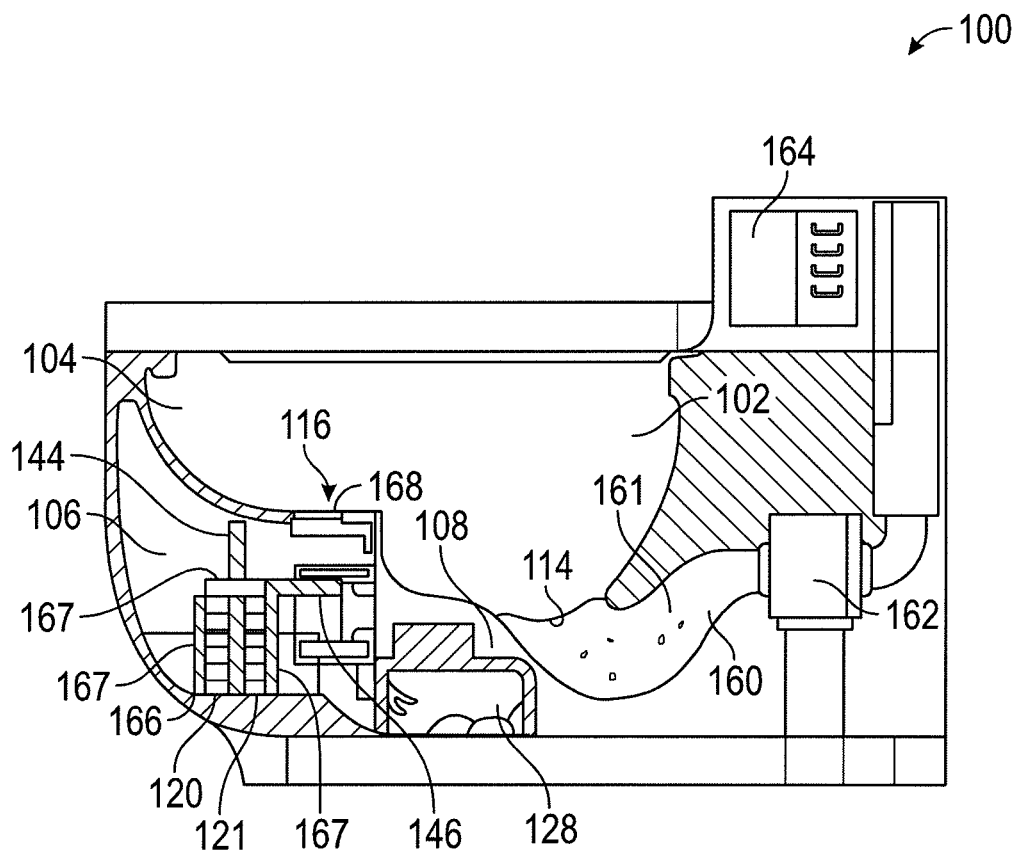
FIG. 3 is a side cross-sectional view of a portion of the collection system 100 of FIG. 1 along the line 3-3 in FIG. 2B.

FIG. 3 is a side cross-sectional view of a portion of the collection system 100 of FIG. 1 along the line 3-3 in FIG. 2B. The collection system 100 includes the waste receptacle 102, the capture area 104, the collection area 106, the storage area 108, the drain 114, the port 116, the stack 121 of collection units 120, the storage container 128, the shaft 144, and the grasping element 146. In addition, in this example the collection system 100 includes a plumbing system 160, a garbage disposal 162, a power and control unit 164, a collection unit storage 166 and a plug 168.

The plumbing system 160 receives waste (e.g., excess urine, a funnel portion of the collection unit 120 as described below) from the waste receptacle 102 via the drain 114 in order to flush the waste receptacle 102 for subsequent uses. In this example the plumbing system 160 includes a pipe 161 extending from the drain 114 and connected to a sewage system. The garbage disposal 162 receives solid and liquid matter traveling through the pipe 161 and breaks down solid material (e.g., the funnel portion of the collection unit 120 as described below) sufficiently (e.g., automatically and/or by user actuation), such that the solid material can flow through the plumbing system without causing obstructions or other malfunctions.

Figure 10:
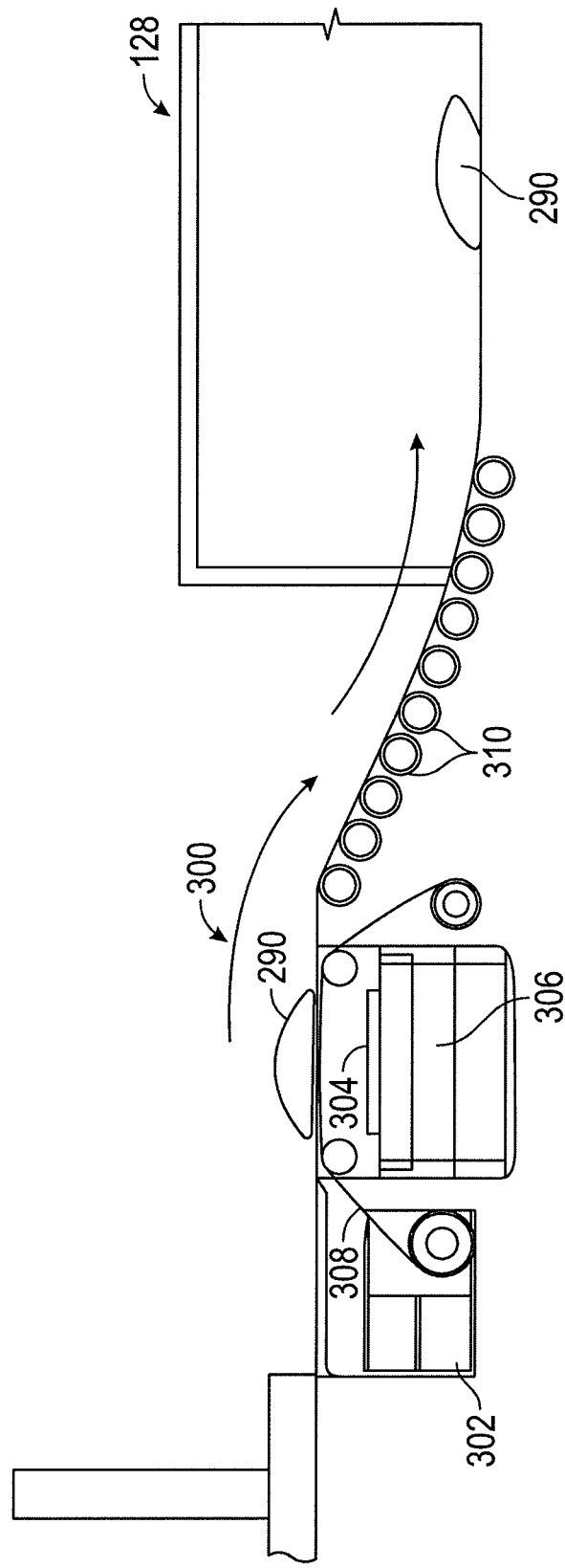
FIG. 10 is a schematic view of the example conveyor of FIG. 9 and the example storage container of FIG. 1.

The power and control unit 164 provides electrical power (e.g., from an outlet, a battery, etc.) to one or more components of the collection system 100 such as the control unit 164 itself, the plug 168, the transport mechanism 122, the sealing mechanism 124, the refrigerated storage container 128, a driver to move the housing unit 110 between a retrieval configuration and an operating configuration, the garbage disposal 162, the air pump 230 (discussed below in connection with FIGS. 7 and 11), the conveyer (discussed below in connection with FIG. 10), and the labeling press 304 (discussed below in connection with FIG. 10).

A controller aspect of the power and control unit 164 includes electronic components, including, e.g., a computer readable storage, a computer processor, one or more programmable circuits (e.g., field-programmable gate arrays) and a user interface (e.g., a touch screen or a screen and key pad combination) by which a human operator can operate (via electrical wiring connected to the controller) the various electrical components of the collection system 100 in the proper sequence (e.g., the plug 168, the transport mechanism 122, the sealing mechanism 124, the refrigerated storage container 128, a driver to move the housing unit 110 between a retrieval configuration and an operating configuration, the garbage disposal 162, the air pump 230 (discussed below in connection with FIGS. 7 and 11), the conveyer 300 (discussed below in connection with FIG. 10), the labeling press 304 (discussed below in connection with FIG. 10), and so forth.

Thus, user inputs to the user interface of the controller produce electrical signals that operate one or more of the various electrical components of the collection system 100. In some examples, an operator of the collection system 100 enters data identifying the subject providing the urine sample (e.g., name, birth date, date of the urine sample), which data is then printed on one or more sealed samples of the subject's urine with the labeling press 304 (FIG. 10).

In some examples, the controller can be programmed to run through multiple urine collection cycles from multiple subjects without human intervention by a human operator prior to retrieval of the collected urine samples from the housing unit 110. In other examples, a human operator operates one or more electrical components of the collection system 100 after each urine collection by utilizing the controller interface. In some examples, the controller aspect of the power and control unit 164 is remote (e.g., in another room) from the rest of the collection system 100, and communicates with the electrical components of the collection system 100 remotely (e.g., via radio frequency signals). The controller aspect can be security enabled, preventing access thereto by unauthorized individuals (e.g., the subject providing the urine sample)

The collection unit storage 166 is configured to hold a plurality of unused collection units 120, e.g., in the form of the stack 121. In the example shown in FIG. 3, the collection unit storage 166 includes a plurality of vertical supports 167, the horizontal space between the supports 167 sized to hold the stack 121 of collection units 120. In some examples, a vertically oriented biasing mechanism (e.g., a spring) at the bottom of the collection unit storage 166 applies an upward biasing force against the weight of the collection units 120, such that the uppermost collection unit 120 is at or approximately the same height for capture by the transport mechanism 122 for successive urine collection cycles, i.e., even as collection units 120 are used up to collect urine samples.

The plug 168 is sized and configured to reversibly plug the port 116, providing a fluid-proof seal that, when plugging the port 116, prevents fluid from passing from the capture area 104 through the port 116 into the collection area 106. In some examples the plug 168 includes a gasket or other sealing means. The plug 168 is movable between a plugged position and an unplugged position. When the plug 168 is in the plugged position, in some examples the collection system 100 can be used as a toilet. When the plug 168 is in the unplugged position, the collection system 100 can be used to collect one or more urine samples. The plug can be moved between the plugged and unplugged position manually, or alternatively, with an electrically powered driver.

FIG. 4A is a top view of a portion of the collection system 100 of FIG. 1, illustrating the grasping element 146 of the transport mechanism 122 in a first position. FIG. 4B is a top view of a portion of the collection system 100 of FIG. 1, illustrating the grasping element 146 of the transport mechanism 122 in a second position. FIG. 4C is a top view of a portion of the collection system 100 of FIG. 1, illustrating the grasping element 146 of the transport mechanism 122 in a third position. With reference to FIG. 4, the collection system 100 includes the collection area 106, the storage area 108, the housing unit 110, the port 116, the collection units 120, the transport mechanism 122, the waste area 126, the housing unit base 142, the shaft 144, the grasping element 146, and the plug 168. In addition, in this example, the collection system 100 includes a driver 170, a plug arm 172, a transport arm 174, an extension 176, and a grasper pivot 178, and the collection units 120 each have a projection 180 and a valve 182.

The driver 170 is coupled to the plug 168 and moves the plug into and out of the plugged position with the plug arm 172. In some examples, the plug arm 172 is capable of both up and down movement and side to side (and/or front to back movement). Up and down movement of the plug arm 172 allows for the plug 168 to be inserted upward and into, and removed downward from, the port 116. Side to side (and/or front to back) movement allows the plug to of positioned out of the movement path of the transport mechanism 122.

The transport arm 174 is rotatably coupled to the shaft 144. In some examples, the extension 176 is movably coupled to the transport arm 174, allowing for radial extension and retraction of the transport arm 174 relative to the longitudinal axis of the shaft 144. In other examples, the extension 176 is fixedly coupled to the transport arm 174, such that the transport arm 174 maintains a constant radius relative to the longitudinal axis of the shaft 144. The grasping element 146 projects radially from the extension 176. In some examples a pivot 178 at the junction between the grasping element 146 and the extension allows the fingers 179 of the grasping element 146 to open and close about a collection unit 120 for picking up and transporting a collection unit 120.

Figure 11:
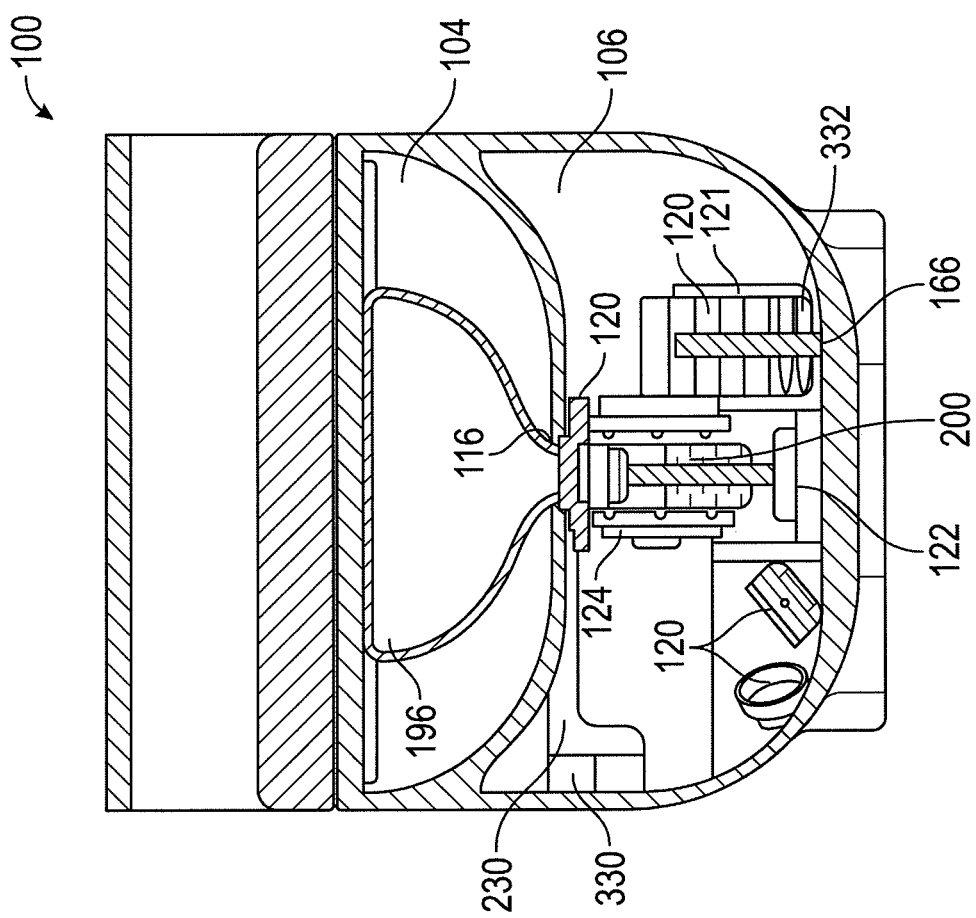
FIG. 11 is a front view of a portion of the example urine collection system of FIG. 1, illustrating the urine collection system at a time when urine is being collected from a subject.

Each of the collection units 120 has a projection 180 for mating with an air pump 230 (FIG. 11). A one way valve 182 disposed in the projection 180 is configured to mate with a nozzle of an air pump, which opens the valve, allowing airflow into the interior of the collection unit 120, as described in greater detail below.

With reference to FIG. 4A, the transport mechanism 122 is in a first position, with the transport arm 174 extending toward the stack 121 (FIG. 1) of collection units 120, such that the fingers 179 of the grasping element 146 are positioned to grasp the upper most collection unit 120 on the stack 121. At the same time, the plug 168 is in position in the port 116, plugging the port 116.

With reference to FIG. 4B, the transport arm 174 has rotated (relative to FIG. 4A) about the shaft 144 in a counterclockwise direction, carrying the uppermost collection unit 120 until it is aligned with the port 116. Before or while the transport arm 174 is rotating to this position, the driver 170 causes the plug arm 172 to lower the plug down from the port 116, and then rearwards such that the plug 168 is no longer aligned with the port 116. It should be appreciated that in alternative configurations, the plug's transport arm is 174 disposed above the collection area 106 (e.g., in the capture area 104), and the plug 168 can be moved downwards into position in the port 116, and upwards to remove the plug 168 from the port 116.

Once the collection unit 120 is vertically aligned with the port 116, the transport mechanism raises the collection unit 120 (upwards along the shaft 144) into the port 116, creating a seal therebetween. At this time, air is pumped into the collection unit 120 as described below in connection with FIGS. 6-7.

As illustrated in FIG. 4C, once the urine sample or samples have been collected from an individual subject, the transport arm 174, carrying the used collection unit 120 in the grasping element 146, again rotates in the counterclockwise direction until it is vertically aligned with the waste area 126. Once aligned in this manner, the grasping element 146 releases the used collection unit 120 (e.g., by pivoting open the fingers 179 of the grasping element 146 about the pivot 178), thereby dropping the used collection unit into the waste area 126. In some examples (including that shown in FIG. 4C), upon rotation of the transport arm 174 away from the port 116 following urine collection, the driver 170 causes the plug arm 172 to move the plug 168 forward and upward back into position in the port 116, thereby plugging the port 116 until another urine collection is to be performed with the collection system 100. However, in some examples, the port 116 can remain open following rotation of the transport arm 174 away from the port 116, thereby keeping the collection system 100 in a configuration ready for a subsequent urine collection.

Following release of the used collection unit 120, the transport arm 174 can be rotated clockwise (or, in some examples, counterclockwise for a full 360° rotation) until it is back in the first position shown in FIG. 4C to grasp the uppermost collection unit 120 in preparation for the next urine collection cycle. As discussed above, in some examples a biasing mechanism positioned below the stack of unused collection units 120 balances the weight of the stack such that the uppermost collection unit 120 in the stack is always in the same vertical position for grasping by the grasping element 146.

Figure 5A:
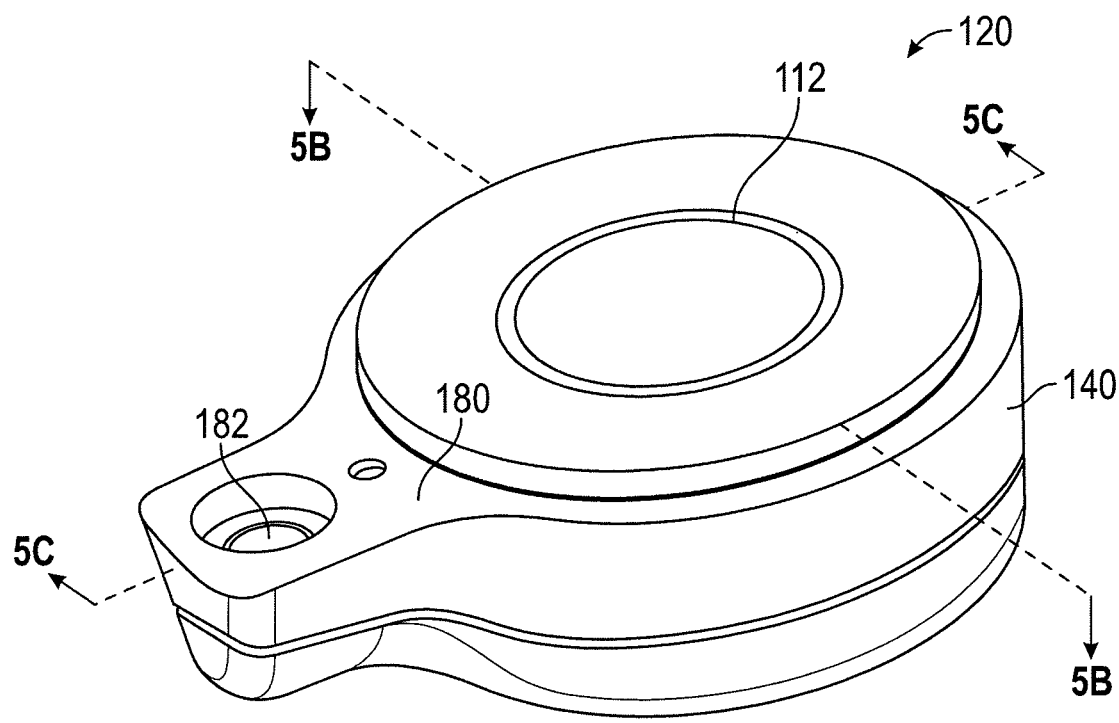
FIG. 5A is a top perspective view of the example collection unit of FIG. 1.
Figure 5B:
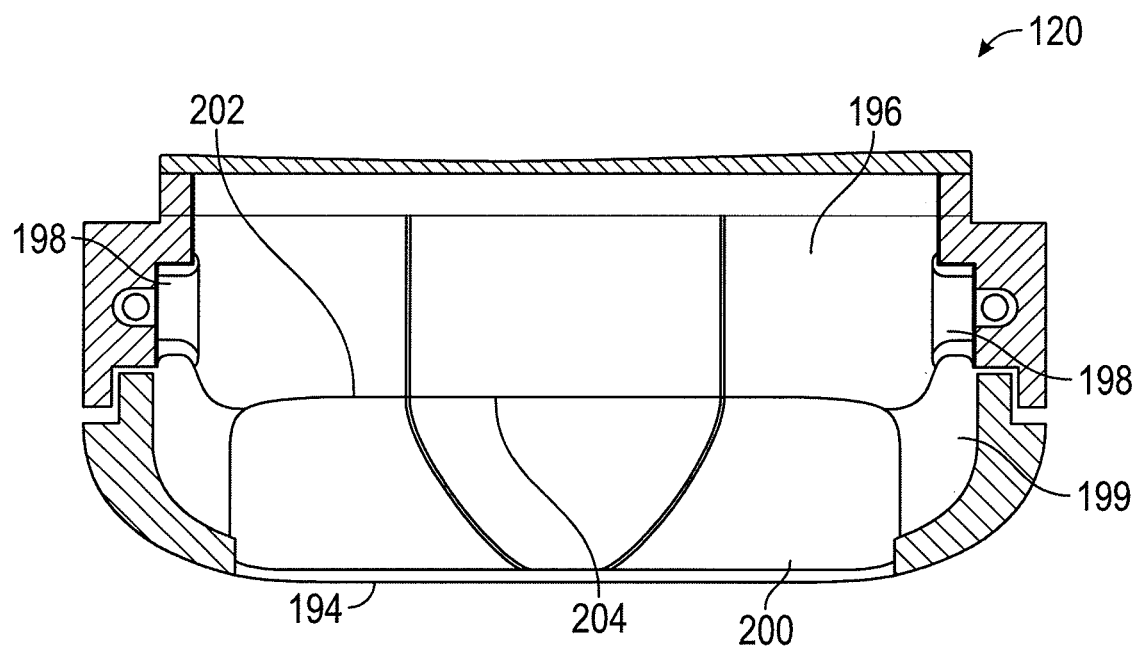
FIG. 5B is a cross-sectional view of the collection unit of FIG. 5A along the line 5B-5B in FIG. 5A.
Figure 5C:
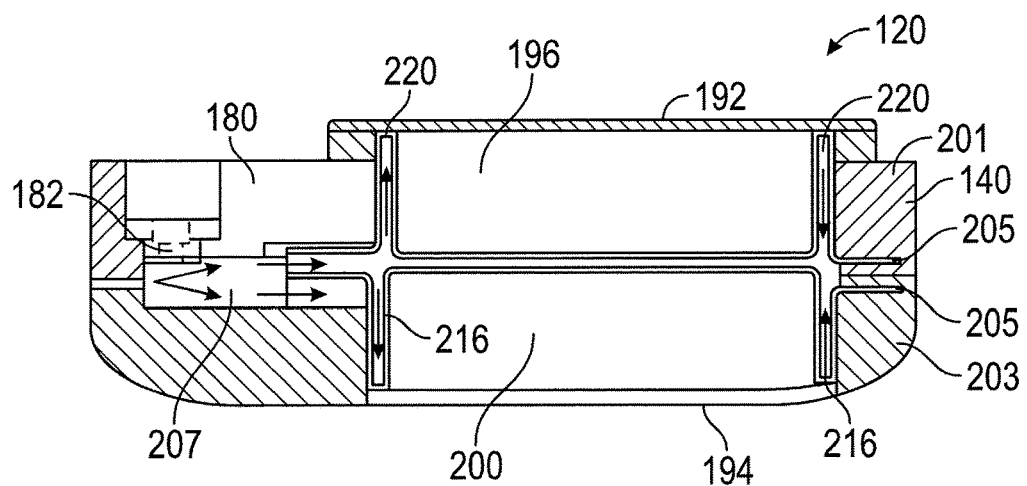
FIG. 5C is a cross-sectional view of the collection unit of FIG. 5A along the line 5C-5C in FIG. 5A.

FIG. 5A is a top perspective view of an example collection unit 120 of FIG. 1. FIG. 5B is a cross-sectional view of the collection unit 120 of FIG. 5A along the line 5B-5B in FIG. 5A. FIG. 5C is a cross-section view of the collection unit 120 of FIG. 5A along the line 5C-5C in FIG. 5A. With reference to FIGS. 5A, 5B and 5C, the collection unit 120 includes the casing 140, the projection 180 and the valve 182 as described above. In addition, in this example the collection unit 120 includes a top seal 192, a bottom seal 194, a funnel 196, one or more overflow spouts 198, and a vessel 200.

FIGS. 5A, 5B, and 5C all illustrate the collection unit 120 in a sealed configuration, i.e., with the top seal 192 and the bottom seal 194 intact and prior to air being pumped into the interior chamber 199 of the collection unit 120 via the valve 182.

In some examples, the casing 140 is constructed of a relatively strong and rigid material (e.g., a hard plastic), sufficient to force the expansion of the funnel 196 and the vessel 200 through the top seal 192 and the bottom seal 194, respectively, upon inflation of the funnel 196 and the vessel 200, as described in greater detail below.

The top seal 192 and the bottom seal 194 can be constructed of a material (e.g., a relatively thin leaf of aluminum, plastic or the like) that prevents contamination of the funnel 196 and the vessel 200 and that breaks relatively easily upon inflation and expansion of the funnel 196 and the vessel 200. In a particular example, the top seal 192 and the bottom seal 194 are constructed of an aluminum leaf that is less than 0.3 mm in thickness.

As shown in FIG. 5B, the top 204 of the vessel 200 abuts the bottom 202 of the funnel 196, ensuring that the funnel 196 expands upwards from its bottom 202 upon inflation, while the vessel expands downwards from its top 204 upon inflation.

With reference to FIG. 5C, in some examples, the casing 140 includes an upper component 201 that houses the funnel 196, and a lower component 203 that houses the vessel 200. The upper component 201 and the lower component 203 (and likewise the funnel 196 and the vessel 200) can be manufactured separately and then coupled together to form the collection unit 120.

In some examples, the funnel 196 and the vessel 200 are integrated such that a single air channel can pump air into both the funnel 196 and the vessel 200 simultaneously. In the example shown in FIG. 5C, the funnel 196 and the vessel 200 are discrete components and receive pressurized air via discrete, unconnected air channels 216 (with respect to the vessel 200) and 220 (with respect to the funnel 196). Pressurized air enters the air channels 216, 220 via a common conduit 207 leading from the valve 182, the pressurized air following the path of the arrows in FIG. 5C.

In some examples, one or both of the air channels 216, 220 includes a deflation valve 205. The deflation valves 205 open above a threshold pressure in the channels 216, 220, respectively to release air into the environment and thereby prevent over-pressurization (and potentially premature destruction) of the channels 216, 220. Even below the threshold pressure, the deflation valves 205 can provide controlled release of air from the channels 216, 220. In the case of the funnel 196, controlled air release via the deflation valve 205 can help to reduce the size of a used funnel 196 in preparation for safe disposal via the waste receptacle 102 (FIG. 1).

Still with reference to FIG. 5, when the amount of urine evacuated by a subject exceeds a predetermined volume, the excess urine can drain out of the funnel 196 (when inflated) via one or more overflow spouts 198 disposed in a wall of the funnel 196. The overflow spouts 198 are hollow (e.g., tubular) members in fluid communication with the interior of the funnel 196 positioned at a height on the funnel corresponding to a predetermined volume cutoff for urine collection. Excess urine drains through overflow spouts 198 directly into the waste receptacle 102 (FIG. 1).

The vessel 200 is made of a durable, flexible, inflatable, fluid proof material, such as a polyethylene. In some examples the interior surface of the polyethylene is coated with a material suitable for preserving urine. The funnel 196 is made of a flexible, inflatable, fluid proof material that is sewage and septic safe, and/or dissolvable in water, and/or a material that readily disintegrates when processed by the garbage disposal 162 (FIG. 3). In some examples, the funnel 196 is made from a poly vinyl chloride.

Figure 6:
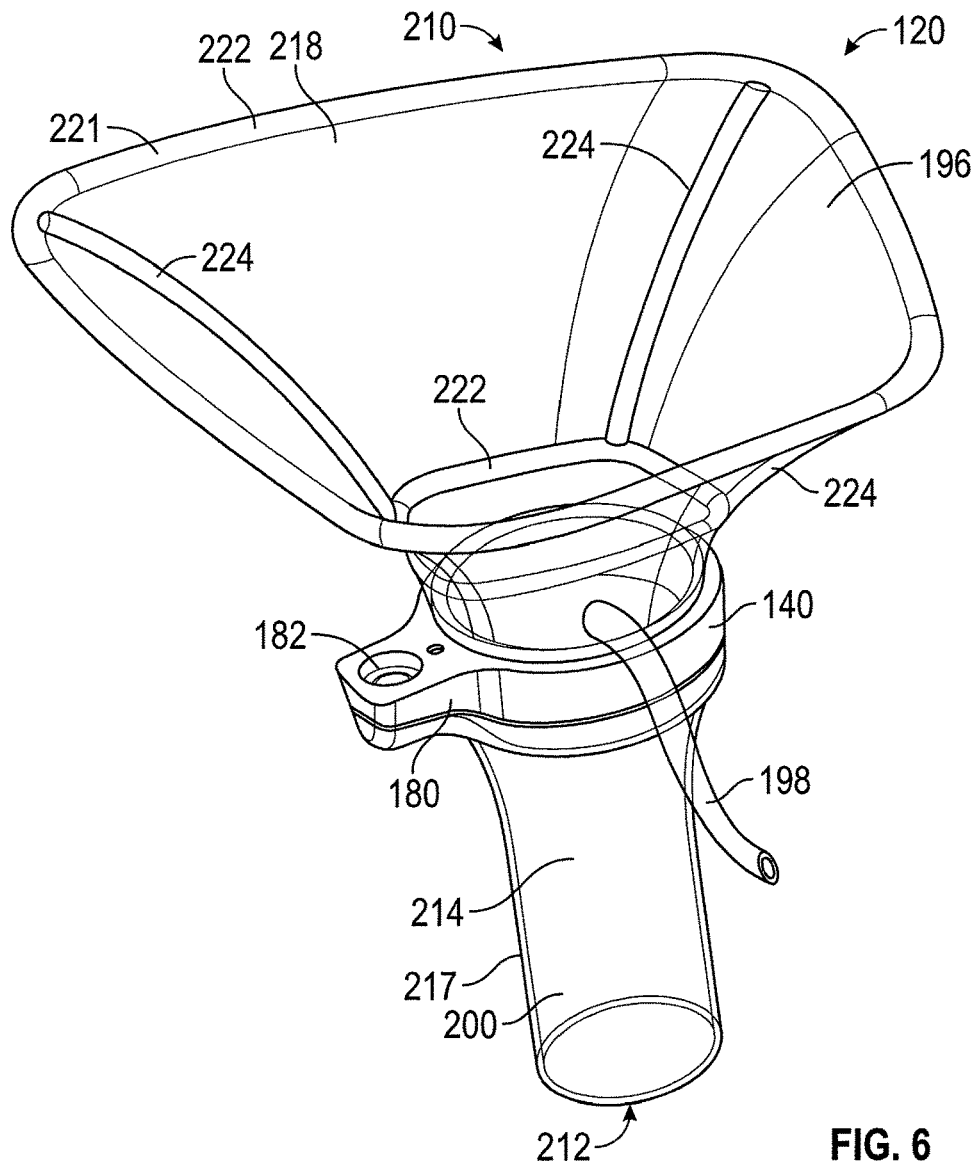
FIG. 6 is a top perspective view of the example collection unit of FIG. 1, the collection unit being in an inflated state.

FIG. 6 is a top perspective view of the collection unit 120 of FIG. 1, the collection unit 120 being in an inflated state. The collection unit 120 includes the casing 140, the projection 180, the valve 182, the funnel 196, the overflow spout 198, and the vessel 200, as discussed above. In addition, in this example, the collection unit 120 is defined by a top 210 and a bottom 212. The vessel 200 has an interior space 214 defined by a skin 217. The funnel 196 includes a skin 218 and a web 221, the web 221 consisting of one or more latitudinal channels 222 and one or more longitudinal channels 224, the longitudinal channels 224 connecting adjacent latitudinal channels. When inflated, the channels 220, 216 of FIG. 5C form, respectively, the web 221 and the skin 217 of FIG. 6.

Air pumped through the valve 182 passes along the conduit 207 (FIG. 5C) into the interior of the sealed collection unit 120. The conduit 207 (FIG. 5C) pipes into the channels 220, (FIG. 5C), which form the web 221 of the funnel 196, causing air pressure expansion of the latitudinal channels 222 and longitudinal channels 224, thereby forcing the web 221 into its expanded shape. Expansion of the web 221 breaks the top seal 192 (FIG. 5) as discussed above as the funnel 196 forms above the port 116 (FIG. 1) to funnel urine evacuated by the subject through the port 116 into the vessel 200. The skin 218 spans the spaces between longitudinal channels 224 and the latitudinal channels 222, thereby forming a complete interior funneling surface.

Alternative constructions for the funnel should be readily appreciated. For example, the web 221 can consist of a flexible, non-inflatable material such as wire that provides a skeleton structure that defines the expanded shape of the funnel 196, while one or more portions of the skin 218 are inflatable via the conduit 207 (FIG. 5C) for the purpose of generating the expansion through the top seal 192.

As the funnel 196 takes shape upon expansion of the web 221, the one or more overflow spouts 198 deploy, ending in the capture area 104 (FIG. 1) such that excess urine ultimately runs off into the waste receptacle 102 (FIG. 1).

As air is pumped through the valve 182 into the interior of the sealed collection unit 120 via the conduit 207 (FIG. 5C), the rising air pressure in the channels 216 (FIG. 5C) also causes the vessel 200 to expand and breach the bottom seal 194 (FIG. 5), forming the interior space 214 defined by the skin 217 below the port 116 (FIG. 1). Thus, one or more portions of the skin 217 is/are inflatable (e.g., having an inner layer and an outer lower with an air-fillable space therebetween). In alternative examples, the pumped air applies pressure to the surface of the skin 217 immediately surrounding the interior space 214, thereby pushing the skin downward to form the vessel 200.

In some examples the expanded vessel 200 (shown in FIG. 6) is prefabricated with graduated markings to indicate volume increments for the collection of multiple urine samples from a single subject. In some examples, the expanded vessel 200 includes one or more test components that indicate the presence of one or more compounds or chemicals in the collected urine upon initial or extended contact therewith.

Figure 7A:
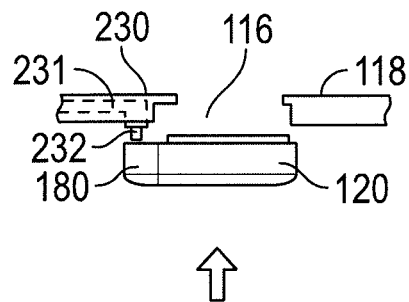
FIG. 7A is a representative side view of an example collection unit of FIG. 1 prior to being positioned in the port 116 of FIG. 1.
Figure 7B:
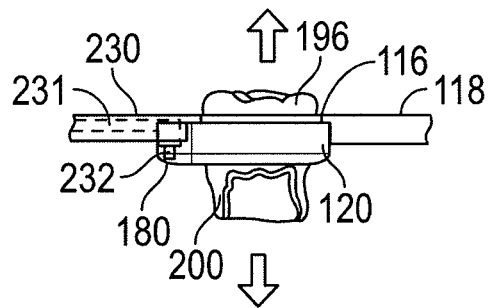
FIG. 7B is a representative side view of the collection unit of FIG. 7A after it has been positioned in the port 116 and connected to an air pump for a period of time.
Figure 7C:
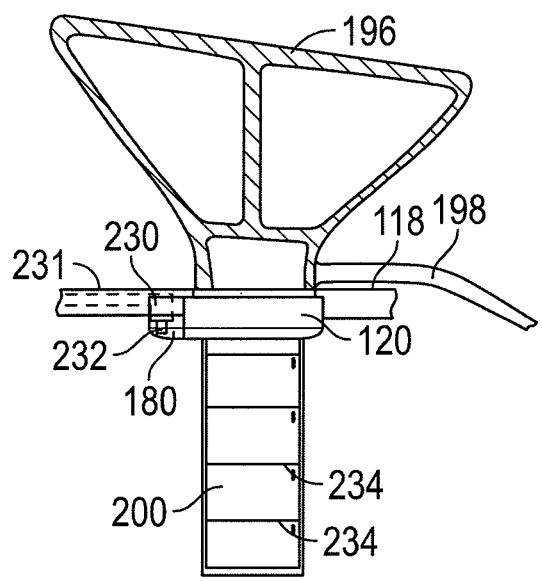
FIG. 7C is a representative side view of the collection unit of FIG. 7A a period of time after that shown in FIG. 7B.
Figure 7D:
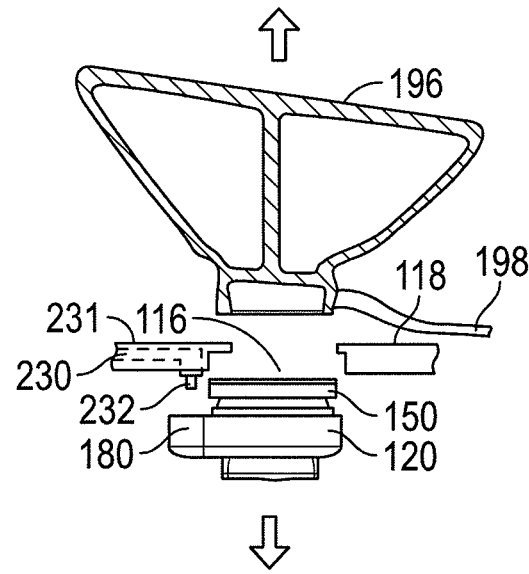
FIG. 7D is a representative side view of the collection unit of FIG. 7A a period of time after that shown in FIG. 7C.

FIG. 7A is a representative side view of the example collection unit 120 of FIG. 1 prior to being positioned in the port 116 of FIG. 1. FIG. 7B is a representative side view of the collection unit 120 of FIG. 7A after it has been positioned in the port 116 and connected to an air pump for a period of time. FIG. 7C is a representative side view of the collection unit 120 of FIG. 7A a period of time after that shown in FIG. 7B. FIG. 7D is a representative side view of the collection unit 120 of FIG. 7A a period of time after that shown in FIG. 7C.

With reference to FIG. 7, the collection unit 120 includes the projection 180, the funnel 196, the vessel 200, and the overflow spout 198 discussed above. FIG. 7 also shows the port 116 and the sloped surface 118 discussed above. In addition, in this example, the collection system 100 (FIG. 1) includes an air pump 230 having a release port 232 through which air is pumped into the collection unit 120, the release port 232 capable of opening the valve 182 (FIG. 6) when mated therewith in the projection 180. In addition, the vessel 200 has graduated markings 234 for measuring multiple urine samples from a single subject, as described above. With reference to FIG. 7D, a secondary sealing mechanism 250 is also shown.

With reference to FIGS. 7A and 7B, upon coupling of the sealed collection unit 120 to the port 116 (see arrow in FIG. 7A), an arm 231 of the air pump 230 is moved into place and mated with the collection unit 120 via the valve 182 (FIG. 6) in the projection 180. In some examples, the arm 231 of the air pump 230 is stationary in a position aligned with the projection 180 such that engagement of the valve 182 by the air pump 230 is automatically achieved upon introduction of the collection unit 120 into the port 116; in accordance with these examples, the air pump automatically disengages from the valve 182 upon lowering of the collection unit 120 from the port 116. Upon engagement of the valve 182 by the air pump 230, air is then pumped into the funnel 196 and the vessel 200, causing expansion thereof (see the arrows in FIG. 7B), as described above, until both are fully expanded as shown in FIG. 7C.

Following collection of urine from the subject in the vessel 200 and severing of the sealed urine sample(s) from the vessel 200 (described below in connection with FIG. 9), as shown in FIG. 7D, the air pump arm 231 is decoupled from the collection unit 120, and the collection unit is lowered (see lower arrow in FIG. 7D) from the port 116 until a lower portion of the funnel 196 is aligned with the secondary sealing mechanism 250. The secondary sealing mechanism 250 seals off the portion of the collection unit 120 below it, and severs the funnel 196, which deflates and can be disposed of (see upper arrow in FIG. 7D) via the waste receptacle 102 (FIG. 1). See the arrows in FIG. 7C. What remains of the collection unit 120 can then be transferred to the waste area 126 in the manner described above in connection with FIG. 4.

Figure 8A:
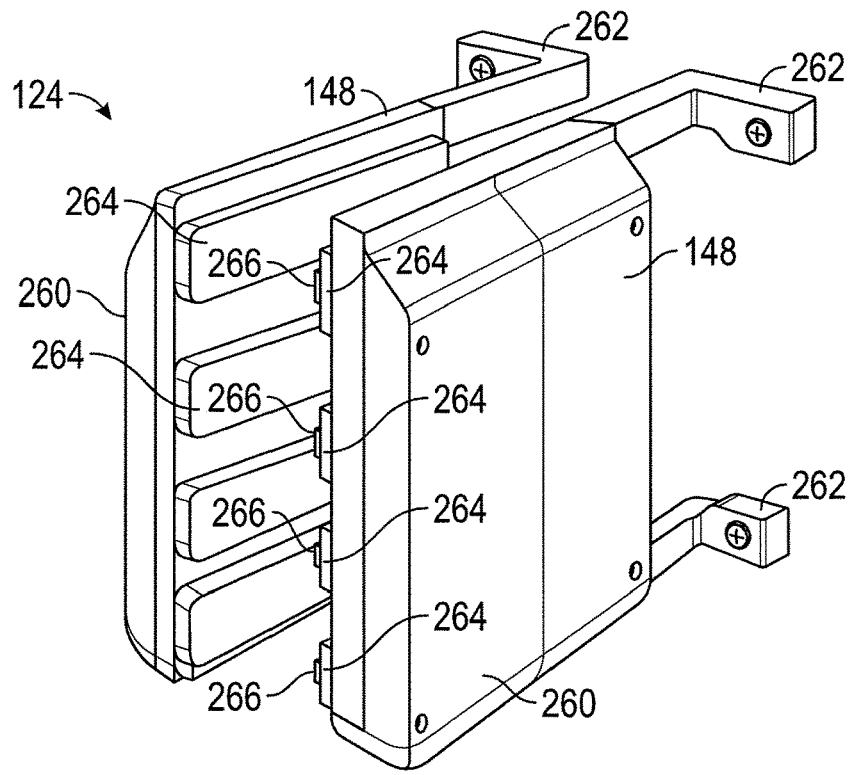
FIG. 8A is a perspective view of the example sealing mechanism of FIG. 1.
Figure 8B:
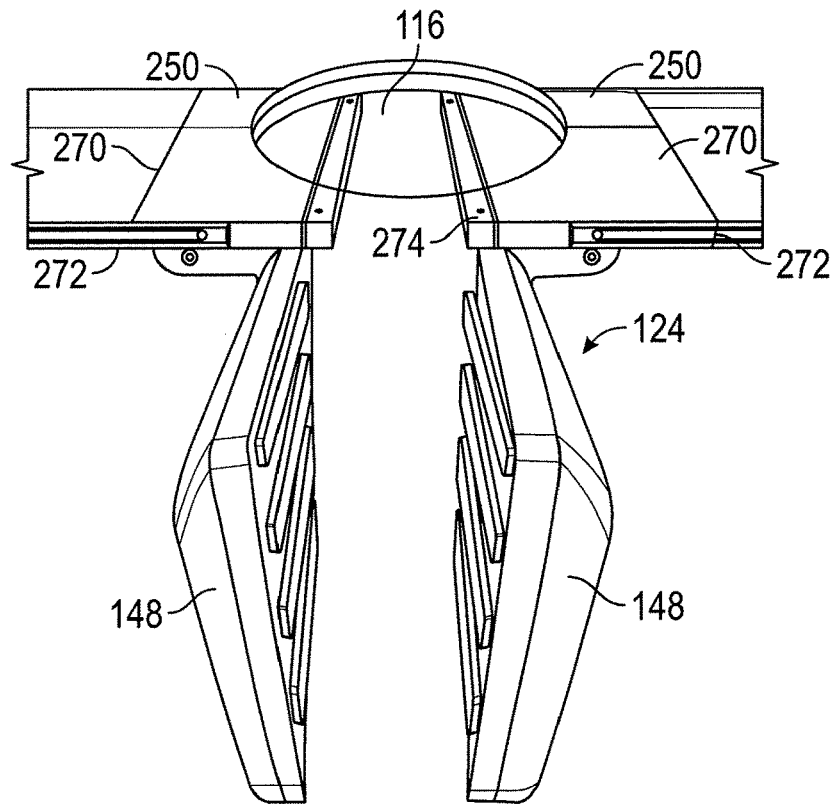
FIG. 8B is a further perspective view of the example sealing mechanism of FIG. 1 and the example secondary sealing mechanism of FIG. 7.

FIG. 8A is a perspective view of the sealing mechanism 124 of FIG. 1. FIG. 8B is a further perspective view of the sealing mechanism 124 of FIG. 1 and the secondary sealing mechanism 250 of FIG. 7 positioned below the port 116 of FIG. 1. With reference to FIG. 8, the sealing mechanism 124 includes the first and second arms 148 as discussed above. In addition, in this example, each of the arms 148 includes a housing 260 and one of the arms 148 includes one or more heating elements 266; both of the arms 148 include mounting brackets 262 and one or more retractable projections 264, the retractable projections 264 of one arm 148 horizontally aligning with the retractable projections 264 of the other arm 148.

The brackets 262 mount the arms 148 in parallel configuration to a surface or other structural feature(s) of the collection area 106 (FIG. 8). The housing 260 in each arm 148 contains a motive element (e.g., a solenoid) configured to extend and retract the retractable projections horizontally from the arms 148 (i.e., towards or away from the retractable projections 264 disposed in the other arm 148). In addition, in at least one of the arms 148, component within the housing 260 provides electric current to the heating elements 266 to heat them via electrical resistance. In some examples, the heating elements 266 include one or more electrical resistors and are disposed on the retractable projections 264. It should be appreciated that the number and placement of the retractable projections 264 and the heating elements 266 can be varied according to specific needs. The number of retractable projections dictates the number of discrete urine samples that can be collected from a single subject's evacuation. It should also be appreciated that the heating elements 266 can be disposed on both arms 148 in a variety of suitable configurations. Similarly, in some alternative examples only one of the arms 148 includes retractable projections capable of sufficient extension to close the gap between the two arms 148.

With reference to FIG. 8B the secondary sealing mechanism 250 is disposed above the first sealing mechanism 124 and below the port 116. In this example, the secondary sealing mechanism 250 includes first and second plates 270 that move towards and away from each other (with actuation provided by, e.g., a solenoid), the plates 270 coupled to, and moving along, a track 272. A heating element 274 (which can be heated by, e.g., a solenoid) is disposed on the edge of one or both plates 270 that faces the other plate 270.

FIG. 9A is a side view representation of the example sealing mechanism 124 and the collection unit 120 of FIG. 1 at a first time following collection of a subject's urine. FIG. 9B is a side view representation of the example sealing mechanism 124 and the collection unit 120 of FIG. 1 at a second time following the first time of FIG. 9B. FIG. 9C is a side view representation of the example sealing mechanism 124 and the collection unit 120 of FIG. 1 at a third time following the second time of FIG. 9B. FIG. 9D is a side view representation of the example sealing mechanism 124 and the collection unit 120 of FIG. 1 at a fourth time following the third time of FIG. 9C.

With reference to FIG. 9, the sealing mechanism 124 includes the arms 148, the retractable projections 264 and heating elements 266 as discussed above; the collection unit 120 includes the funnel 196 and the vessel 200, the vessel 200 containing a subject's urine. Also shown are the air pump 230, the port 116, the plug 168 and the plug arm 172. In addition, with reference to FIG. 9B, in this example a conveyor 300 is disposed under the sealing mechanism and vertically aligned with the port 116.

With reference to FIG. 9A, at a first time, following collection of the urine in the vessel 200, the collection unit 120 is in place in the port 116, the air pump 230 is hooked up to the collection unit 120, and the retractable projections 264 extend out and pinch the vessel 200 in one or more locations. The one or more heating elements 266 seal the vessel 200 at one or more locations and cut the vessel 200 into one or more discrete sealed packets 290 of urine. In some examples, the heating element 266 cuts the vessel 200 by melting it at the point of sealing. In other examples, another cutting component, e.g., one or more blades, is employed for this purpose.

In some examples, optical sensors or other sensors disposed on the arms 148 detect when sufficient urine has been collected beneath each pair of corresponding retractable projections 264 for a complete urine sample, causing a signal to be sent to the respective pair of retractable projections to extend and seal the urine below into a packet 290.

In some examples, one or more temperature sensors disposed on or near the sealing mechanism 124 measures the temperature of the urine collected in one or more of the packets 290, e.g., by measuring the temperature of the exterior of the vessel 200 that the forms the packet 290. Measuring a urine sample's temperature can help to detect tampering or fraud by the subject providing the urine sample, as a sample that is hotter or colder than the typical temperature range for recently evacuated urine can indicate that the subject has not provided a contemporaneous sample of their own urine. In some examples, temperature information measured by the one or more temperature sensors can be fed to the printer 302 (directly, or via the controller discussed above; see FIG. 10), and the temperature reading can be printed on a label placed on the sealed packet 290 containing the corresponding urine sample (see FIG. 10).

With reference to FIG. 9B, at a second time subsequent to the first time, the collection unit 120 remains in place in the port 116, and the corresponding pairs of retractable projections 264 retract in sequence, starting from the lowest pair and moving upwards. With each retraction a discrete sealed and cut packet of urine 290 drops onto the conveyor 300, which labels each packet 290 and transports each packet 290 into the storage area 108.

With reference to FIG. 9C, at a third time subsequent to the second time, all of the corresponding pairs of retractable projections 264 have retracted, separating all of the discrete packets of collected urine 290 from the vessel 200. In addition, the remainder of the collection unit has been lowered down from the port 116 and the secondary sealing mechanism 250 seals and cuts the bottom of the funnel 196. Depending on the size of the evacuation, following some urine evacuations this can leave a sealed waste pod 292 of excess, uncollected urine in the remaining portion of the collection unit 120, the sealed waste pod 292 defined by a sealed lower portion of the funnel 196 and a sealed upper portion of the vessel 200.

With reference to FIG. 9D, at a fourth time subsequent to the third time, the collection unit 120 is moved horizontally away from the port 116 until it is aligned with the waste area 126 (FIG. 1), where it is dropped along with the waste pod 292. In addition, the funnel 196 with any extra urine it may contain has been released by the secondary sealing mechanism 250 into the capture area 104 (FIG. 1) such that it can ultimately be flushed via the waste receptacle 102 (FIG. 1). In addition, the plug 168 has been moved, with the plug arm 172, back into position in the port 116.

FIG. 10 is a schematic view of the conveyor 300 of FIG. 9 and the storage container 128 of FIG. 1. The conveyor 300 is disposed in the collection area 106 (FIG. 1) below the port 116 (FIG. 1).

With reference to FIG. 10, the printer 302 is instructed (e.g., by the electronic controller) to print subject-specific information (that is, information regarding the subject providing the urine sample) on a label. The printer 302 deposits the printed label on the moving belt 308. The moving belt 308 moves the label into position under the port 116 (FIG. 1), thereby aligning the label with the sealed packet 290 upon its release from the vessel 200. The sealed packet 290 lands on the label on the belt 308. At this time, the solenoid 306 drives a press 304 that applies the label (e.g., via an adhesive on the label) to the packet 290. Following application of the label to the packet 290, the moving belt 308 transfers the labeled and sealed packet 290 onto the sequence of rollers or the conveying means 310, which transport (e.g, via the force of gravity), the packet 290 through an opening in the storage container 128 into the storage container 128. Once of all the subject's packets 290 have been labeled and deposited in the storage container 128, the printer 302 can be reprogrammed with identifying information corresponding to the next subject, and the subsequent urine collection cycle can commence.

FIG. 11 is a front view of a portion of the urine collection system 100 of FIG. 1, illustrating the urine collection system 100 at a time when urine is being collected from a subject. The urine collection system 100 includes the capture area 104, the collection area 106, the port 116, the collection units 120 (including sealed, in-use, and disposed collection units), the stack 121 of sealed collection units 120, the transport mechanism 122, the sealing mechanism 124, the collection unit storage 166, the funnel 196, the vessel 200 and the air pump 230, as discussed above. In addition, in this example, the air pump 230 includes a compressor 330 that is secured to an inner side of the collection area 106, and a biasing mechanism 332 (discussed above) is illustrated below the stack 121 of collection units 120 in the collection unit storage 166.

Figure 12:
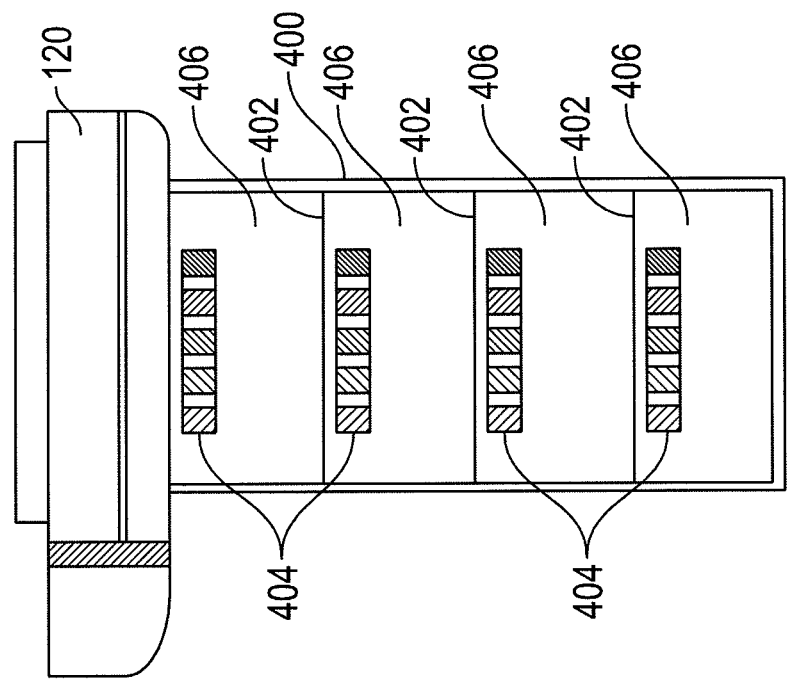
FIG. 12 is a schematic view of an example collection unit in accordance with the present disclosure including an alternative embodiment of a vessel.

FIG. 12 is a schematic view of the collection unit 120 having an alternative embodiment of a vessel 400. The vessel 400 includes graduated markings 402 corresponding to a predetermined volume of urine for each of four urine sample packets 406. The graduated markings 402 likewise correspond to the appropriate sealing and cutting point for aligning with the heating elements 266 and retractable projections 264 of the sealing mechanism 124 (FIG. 8). Within each of the four urine sample packet areas 406 defined by the graduated markings 402, a urine test strip 404 is adhered inside the vessel 200, the test strip 404 being configured to test for at least one chemical or compound in the urine sample.

While the above is a complete description of certain embodiments of the invention, various alternatives, modifications, and equivalents may be used. Therefore, the above description should not be taken as limiting the scope of the invention which defined by the appended claims.

What is claimed is:

1. A system for collecting one or more biomaterials, the system comprising:
 a capture area having a port;
 a collection area disposed below the capture area;
 a collection unit configured to have at least a first configuration and a second configuration, the collection unit being couplable to a pump for transforming the collection unit from the first configuration to the second configuration, the collection unit including a casing, an inflatable funnel, and an inflatable vessel, the casing having an upper component and a lower component, wherein the collection unit is configured such that when the collection unit is in the first configuration, the upper component houses the inflatable funnel, the lower component houses the inflatable vessel, and the collection unit is positioned entirely below the port, and wherein the collection unit is configured such that when the collection unit is in the second configuration, the inflatable vessel is at least partially disposed below the port, and the inflatable funnel extends above the port; and
 a sealer including a plurality of arms disposed in the collection area, the arms being configured to seal the vessel following collection of the one or more biomaterials in the vessel.

2. The system of claim 1, wherein the arms include an extendable and retractable heated projection configured to seal and cut the inflatable vessel.

3. The system of claim 2, wherein the arms are configured to seal and cut the inflatable vessel into a plurality of sealed packets containing the one or more biomaterials.

4. The system of claim 1, further comprising a transporter disposed in the collection area and a collection unit storage, the transporter including at least one finger and being configured for grasping the collection unit and transporting the collection unit between a first position in which the collection unit is aligned with the collection unit storage and a second position in which the collection unit is aligned with the port.

5. The system of claim 4, further comprising a waste area disposed in the collection area, and wherein the transporter is further configured to transport the casing to a third position in which the casing is aligned with the waste area.

6. The system of claim 4, further comprising a storage container and a housing unit, the housing unit housing the storage container and the collection area, and wherein the storage container is slidable relative to the housing unit.

7. The system of claim 4, wherein the collection unit storage is configured to store a plurality of collection units, the collection unit storage further comprising a biasing mechanism.

8. The system of claim 4, wherein the transporter further comprises a base, a shaft extending vertically from the base, and an arm extending radially from the shaft, and wherein the at least one finger is coupled to the arm extending radially from the shaft.

9. The system of claim 8, wherein the at least one finger is configured for both rotational movement and transverse movement relative to the shaft.

10. The system of claim 1, further comprising a plug, the plug being removably positioned in the port.

11. The system of claim 1, wherein the collection unit comprises a projection including an inflation channel, and wherein the projection is configured such that the pump is couplable to the projection.

12. The system of claim 11, wherein the projection includes a valve.

13. The system of claim 1, wherein the inflatable vessel comprises a plurality of test strips for testing the one or more biomaterials for a presence of at least one compound.

14. A system for collecting one or more biomaterials, the system comprising:
 a collection unit configured to have at least a first configuration and a second configuration, the collection unit being couplable to a pump for transforming the collection unit from the first configuration to the second configuration, the collection unit including a casing, an inflatable funnel and an inflatable vessel, the inflatable vessel extending from a top end of the inflatable vessel to a closed bottom end of the inflatable vessel along an elongate dimension of the inflatable vessel, the casing including an upper component configured to house the inflatable funnel when the collection unit is in the first configuration, and a lower component configured to house the inflatable vessel when the collection unit is in the first configuration, the casing further including a projection defining an inflation channel in communication with the inflatable vessel for inflating the inflatable vessel; and
 a sealer including a plurality of arms configured to seal the inflatable vessel following collection of the one or more biomaterials in the inflatable vessel,
 wherein the inflatable vessel includes a skin having an inner surface that defines an interior space of the inflatable vessel, the inner surface being continuous at the bottom end of the inflatable vessel and forming the closed bottom end of the inflatable vessel, the inner surface being configured to collect within the interior space the one or more biomaterials that pass through the funnel into the inflatable vessel through the top end of the inflatable vessel;
 wherein the collection unit is configured such that, in the second configuration,
  (i) the funnel extends upward through a first opening defined by a top end of the upper component; and
  (ii) the vessel extends downward through a second opening defined by a bottom end of the lower component.

15. The system of claim 14, further comprising an air pump for pumping air into the inflation channel to transform the collection unit from the first configuration to the second configuration.

16. The system of claim 14, wherein the plurality of arms include an extendable and retractable heated projection configured to seal and cut the inflatable vessel.

17. The system of claim 16, wherein the plurality of arms are configured to seal and cut the inflatable vessel into a plurality of sealed packets of the one or more biomaterials.

18. The system of claim 14, wherein the projection includes a valve.

19. A system for collecting one or more biomaterials, the system comprising:
- a capture area having a port;
- a collection area disposed below the capture area;
- a pump;
- a collection unit configured to have at least a first configuration and a second configuration, the collection unit being couplable to the pump for transforming the collection unit from the first configuration to the second configuration, the collection unit including a casing, an inflatable funnel, and an inflatable vessel, the casing having an upper component and a lower component, wherein the collection unit is configured such that when the collection unit is in the first configuration, the upper component houses the inflatable funnel, the lower component houses the inflatable vessel, and the collection unit is positioned entirely below the port, and wherein the collection unit is configured such that when the collection unit is in the second configuration, the inflatable vessel is at least partially disposed below the port, and the inflatable funnel extends above the port; and
- a sealer including a plurality of arms disposed in the collection area, the arms being configured to seal the vessel following collection of the one or more biomaterials in the vessel.

\* \* \* \* \*